United States Patent [19]

Bicking

[11] 4,238,487
[45] Dec. 9, 1980

[54] AMINOALKYL BENZOFURAN DERIVATIVES

[75] Inventor: John B. Bicking, Lansdale, Pa.

[73] Assignee: Merck & Co., Inc., Rahway, N.J.

[21] Appl. No.: 89,808

[22] Filed: Oct. 31, 1979

[51] Int. Cl.$^3$ .................. A61K 31/535; A61K 31/34; C07D 307/81

[52] U.S. Cl. .......................... 424/248.52; 424/248.53; 424/250; 424/267; 424/274; 424/285; 544/153; 544/376; 546/196; 260/326.34; 260/346.73

[58] Field of Search ...................... 260/346.73, 326.34; 544/153, 376; 546/196; 424/248.52, 248.53, 250, 267, 274, 285

[56] References Cited

U.S. PATENT DOCUMENTS 3,950,333  4/1976  Durant et al. .................. 260/250 A
4,128,658  12/1978  Price ................................. 260/347.2

FOREIGN PATENT DOCUMENTS 2003471  3/1979  United Kingdom .

Primary Examiner—Henry R. Jiles
Assistant Examiner—Bernard Dentz
Attorney, Agent, or Firm—David L. Rose; Harry E. Westlake

[57] ABSTRACT

There are disclosed novel compounds described as aminoalkyl benzofuran derivatives in which the aminoalkyl benzofuran is connected to a guanidine moiety or functional equivalent thereof through a linear connecting group. Processes for the preparation of such compounds are also disclosed. The compounds are useful for the suppression of gastric acid secretions in mammals and compositions for such uses are also disclosed.

9 Claims, No Drawings

AMINOALKYL BENZOFURAN DERIVATIVES

BACKGROUND OF THE INVENTION

Imidazolylcyanoguanidines in which the imidazole and cyanoguanidine are joined through a linear connecting group are known as H-2 receptor inhibitors. See U.S. Pat. No. 3,950,333 to Durant et al. In addition, compounds have been prepared similar to those of Durant et al in which the imidazole moiety has been replaced by an alkylaminoalkylfuran moiety. See U.S. Pat. No. 4,128,658 to Price et al. The instant compounds differ in utilizing the aminoalkyl benzofuran moiety.

SUMMARY OF THE INVENTION

This invention is concerned with aminoalkyl benzofuran compounds wherein the aminoalkyl benzofuran is connected to a guanidine or guanidine-like moiety through a linear connecting group. Thus, it is an object of this invention to describe such compounds. A further object of this invention is to descrbe processes for the preparation of such compounds. A still further object is to describe the use of such compounds as gastric acid secretion inhibitors in mammals. Further objects will become apparent from a reading of the following description.

DESCRIPTION OF THE INVENTION

The compounds of this invention are best realized in the following structural formula:

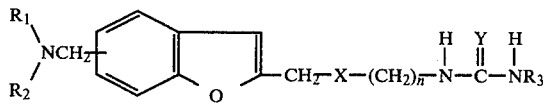

wherein $R_1$ and $R_2$ are independently loweralkyl of from 1-3 carbons and $R_1$ and $R_2$ may be joined to form together with the nitrogen atom to which they are attached, a 5- or 6-membered heterocyclic ring, which may optionally contain another hetero atom selected from oxygen or N-$R_4$ wherein $R_4$ is hydrogen or loweralkyl;

X is sulfur or a methylene group;

n is 2,3 or 4;

$R_3$ is hydrogen loweralkyl, cycloloweralkyl, cycloloweralkylloweralkyl, loweralkenyl, loweralkynyl, phenylloweralkyl, hydroxyloweralkyl, loweralkoxyloweralkyl and di(loweralkyl)aminoloweralkyl; and Y is sulfur, =CHNO$_2$ or =NR$_4$ where $R_4$ is nitro, cyano or loweralkylsulfonyl.

In the instant invention, the term "loweralkyl" unless otherwise defined is intended to include those alkyl groups, of either a straight or branched configuration, which contain from 1-5 carbon atoms. Exemplary of such alkyl groups are methyl, ethyl, propyl, iso-propyl, butyl, sec-butyl, pentyl and the like.

The term "loweralkoxy" is intended to include those alkoxy groups of either straight or branched configuration, which contain from 1-5 carbon atoms. Exemplary of such alkoxy groups are methoxy, ethoxy, propoxy, isopropoxy, butoxy, pentoxy and the like.

The term "loweralkenyl" is intended to include those alkenyl groups, of either a straight or branched configuration, which contain from 2-5 carbon atoms. Exemplary of such alkenyl groups are vinyl, allyl, butenyl, 1-methyl-2-butenyl, pentenyl, and the like.

The term "loweralkynyl" is intended to include those alkynyl groups of either straight or branched configuration which contain from 2-5 carbon atoms. Exemplary of such alkynyl groups are ethynyl, propargyl, butynyl, pentynyl and the like. The heterocycle formed when $R_1$ and $R_2$ are joined may be piperidine, or pyrrolidine and the like.

The term "cycloloweralkyl" is intended to include those cycloalkyl groups which contain from 3-6 carbon atoms. Exemplary of such groups are cyclopropyl, cyclobutyl, cyclopentyl and cyclohexyl.

The heterocycle formed by joining $R_1$ and $R_2$ may be piperidine, pyrrolidine, morpholine, piperazine, N-methyl piperazine and the like.

The preferred compounds of the instant invention are realized in the above structural formula when: $R_1$ and $R_2$ are the same and are loweralkyl of from 1-3 carbon atoms;

X is sulfur;

n is 2;

$R_3$ is hydrogen, loweralkyl or loweralkynyl and

Y is =CHNO$_2$, or =N—CN;

Further preferred compounds are realized when;

$R_1$ and $R_2$ are methyl;

X is sulfur;

n is 2;

$R_3$ is hydrogen, methyl, ethyl, or propargyl; and

Y is =CH—NO$_2$ or =N—CN.

The most preferred compounds are those wherein:

$R_1$ and $R_2$ are methyl;

X is sulfur;

n is 2;

$R_3$ is hydrogen or methyl; and

Y is =CH—NO$_2$ or =N—CN.

The compounds according to the invention readily form physiologically acceptable salts. Such salts include salts with inorganic and organic acids such as hydrochlorides, hydrobromides and sulphates. Particularly useful salts of organic acids are formed with aliphatic mono- or di-carboxylic acids. Examples of such salts are acetates, maleates and fumarates. The compounds may also form hydrates.

The compounds according to the invention can be administered orally, topically or parenterally or by suppository, of which the preferred route is the oral route. They may be used in the form of the base or as a physiologically acceptable salt. They will be in general be associated with a pharmaceutically acceptable carrier or diluent, to provide a pharmaceutical composition.

The compounds according to the invention can be administered in combination with other active ingredients, e.g. conventional antihistamines if required. For oral administration the pharmaceutical composition can most conveniently be in the form of capsules or tablets, which may be slow release tablets. The composition may also take the form of a dragee or may be in syrup form. Suitable topical preparation include ointments, lotions, creams, powders and sprays.

A convenient daily dose by the oral route would be of the order of 100 mg. to 1.2 g. per day, in the form of dosage units containing from 20 to 200 mg. per dosage unit. A convenient regimen in the case of a slow release tablet would be twice or three times a day.

Parenteral administration may be by injection at intervals or as a continuous infusion. Injection solutions may contain from 10 to 100 mg./ml. of active ingredient.

For topical application a spray, ointment, cream or lotion may be used. These compositions may contain an effective amount of the active ingredient, for example of the order of 1½ to 2% by weight of the total composition.

The compounds of the present invention may be made by reacting a primary amine of the formula:

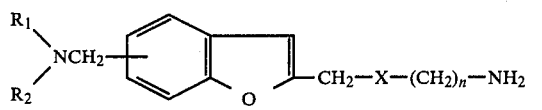

in which $R_1$, $R_2$, n, and X have the meanings given herein with a compound capable of introducing directly or indirectly the group:

in which $R_3$ and Y have the meanings given herein. Compounds which are capable of directly introducing the group:

are, isothiocyanates $R_3NCS$, or compounds of the formula:

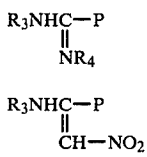

wherein P is a leaving group. The reaction with the isothiocyanate may be carried out by allowing the amine and isothiocyanate to stand in a solvent such as acetonitrile. The reaction between the amine (II) and:

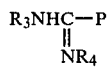

may be carried out in a solvent e.g. ethanol or acetonitrile at ambient or elevated temperatures in the presence of silver nitrate as required. The amine (II) and the compound.

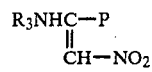

may be stirred in solvents such as ethanol and acetonitrile at ambient or elevated temperatures. Where $R_3$ represents hydrogen, alkali metal cyanates and thiocyanates are used. Examples of leaving groups are halogen, methylthio or alkoxy, preferably methylthio. The introduction of the group:

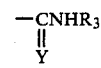

may also be effected indirectly by first reacting the amine (II) with a compound of the formula:

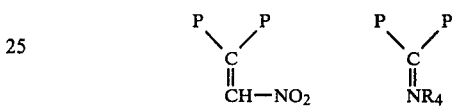

in which P is a leaving group as defined above. This reaction may be effected in a solvent, e.g. ether or acetonitrile at a temperature from ambient to reflux. Treatment of the resulting compound of formula (III):

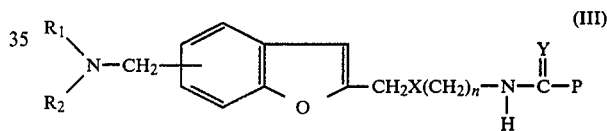

where Y represents $=NR_4$ or $=CH-NO_2$ with a primary amine $R_3NH_2$ at a temperature from ambient to reflux gives the desired end product.

The preferred compounds of this invention wherein Y is a nitromethylene group ($=CHNO_2$) or a cyanoimino group ($=N-CN$) are prepared according to the following reaction scheme:

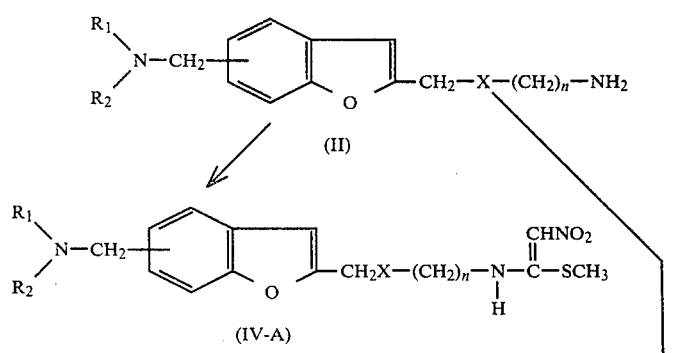

-continued

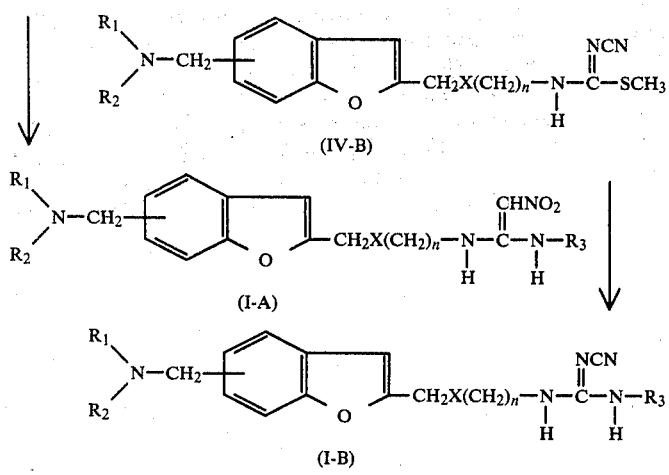

wherein $R_1$, $R_2$, $R_3$, n and X are as defined above.

In the first step of the reaction for the preparation of the nitromethylene compound (I-A), the amine starting material (II) is treated with 1,1-bis-methylthio-2-nitroethene in a suitable solvent, preferably acetonitrile or a lower alcohol, such as ethanol. The reaction may be carried out at about 20° C. to the reflux temperature of the reaction mixture. The reaction is substantially complete in about 8 hours to several days. It is preferred to stir the reaction mixture overnight at about 55°–60° C.

In the first step of the reaction for the preparation of cyanoimino compound (I-B) the amine starting material (II) is reacted with dimethyl cyanodithioimidocarbonate in a suitable solvent, preferably acetonitrile or a lower alcohol, such as ethanol. The reaction may be carried out at about 20° C. to the reflux temperature of the reaction mixture. The reaction is substantially complete in about 1 hour to several days. It is preferred to stir the reaction mixture overnight at about room temperature.

The next step of this reaction sequence is the same for Compounds IVA and IVB and involves the displacement of the methylthio group of Compound IVA and IVB by a loweralkylamino group. A loweralkyl amine is employed and the reaction is carried out by dissolving the amine in a solvent, such as a lower alcohol, preferably ethanol. The reaction is carried out at from 0° C. to the reflux temperature of the reaction mixture. However, where volatile amines are employed the reaction mixture must either be maintained at from 0° C. to room temperature or, if heating is required, the reaction must be placed in a sealed reaction vessel. It is preferred to use atmospheric pressure for the reaction, and to keep the temperature at about room temperature or less. The reaction is complete in about 1 hour to several days, with most reactions requiring stirring overnight. The products (I-A and I-B) are isolated using techniques known to those skilled in this art.

The starting materials (II) wherein X is sulfur are prepared according to the following reaction scheme:

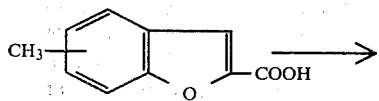

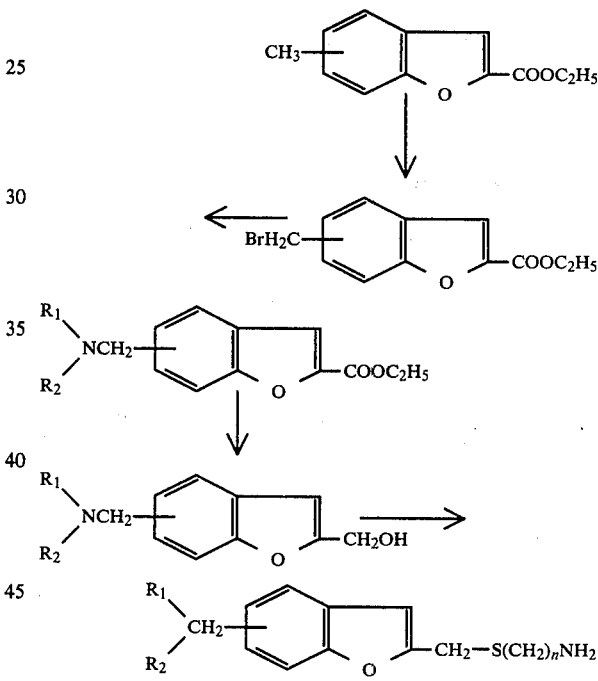

In the above reaction scheme, methylbenzofuran-2-carboxylic acid is esterified using ethanol in the presence of acid to prepare the ethyl ester derivative thereof. The preferred acid is a mineral acid such as sulfuric. The reaction is carried out generally at reflux for from 12 to 36 hours, using ethanol as the solvent.

The methyl group is brominated with a brominating agent, preferably a free radical brominating agent such as N-bromosuccinimide in the presence of a free radical initiator such as α,α'-azobisisobutyronitrile used in catalytic amounts. The reaction is carried out at from 35° C. to the reflux temperature of the reaction mixture and is generally complete in from 2 to 8 hours. An inert solvent, immune to bromination, such as carbon tetrachloride, is employed.

The brominated compound is then treated with an amine to produce the aminomethyl side chain. The reaction is carried out in an inert solvent such as ether, tetrahydrofuran, and the like. The amine reagent is employed in excess, or a separate non-reactive base such as a tertiary amine, is employed to neutralize the liberated hydrogen bromide. The reaction is carried out at from 0° to 30° C. and is generally complete in from 0.5 to 3 hours.

The 2-position ester is then reduced to the hydroxymethyl group using a reducing agent, such as lithium aluminum hydride, lithium borohydride and the like. The reaction is carried out in a solvent immune to reduction such as ether, tetrahydrofuran, and the like. The reaction is carried out at about 5° to 37° C. and generally is complete in from 1 to 3 hours.

The 2-hydroxymethyl benzofuran is then treated with an amino alkyl mercaptan. The reaction is carried out in the presence of acid, generally mineral acid such as concentrated hydrochloric acid at from 5° to 30° C., and is complete in from 20 to 64 hours. The product is isolated using techniques known to those skilled in the art.

The compounds (II) wherein X is a methylene group are prepared according to the following reaction scheme wherein Z is the substituent on the benzo portion of the molecule which may be undergoing reactions simultaneously with the instant synthetic scheme:

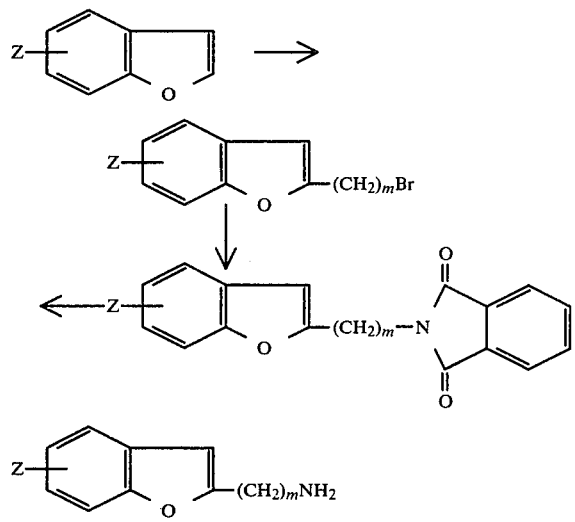

wherein m is 4,5 or 6.

In the foregoing reaction scheme an appropriately substituted benzofuran is lithiated and then treated with a compound $Br(CH_2)_mBr$ where m is as defined above. The reaction is carried out in an inert solvent such as ether, tetrahydrofuran and the like. The benzofuran is added to a solution of lithium diisopropylamide in the solvent in order to prepare the 2-lithium benzofuran intermediate which is then reacted with the dibromo compound. A reaction promoter such as hexamethylphosphoramide is usually present. The reaction is generally carried out at from −20° to 20° C., preferably at about 0° C. and is complete in about 3 to 10 hours.

The bromo compound is then converted to the phthalimide with an alkali metal salt of phthalimide in a solvent such as dimethylformamide at from 20° to 60° C. preferably at room temperature, and is complete in about 12 to 30 hours.

The phthalimido derivative is then cleaved with hydrazine to prepare the amino group. The reaction is carried out at from 25° to 100° C. preferably from about 50° to 75° C., and is complete in about 2 to 24 hours. A solvent such a loweralkanol, preferably ethanol, is employed, and the product is isolated using techniques known to those skilled in the art.

An alternate procedure for the preparation of the alkylaminomethyl substituent on the benzofuran is outlined in the following reaction scheme where Z' is the 2-position substituent which may also be undergoing synthetic reactions simultaneously with the instant synthetic scheme:

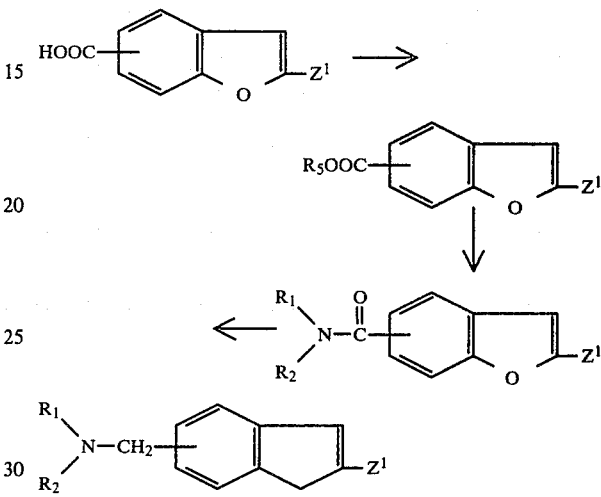

wherein $R_1$ and $R_2$ are as previously defined and $R_5$ is loweralkyl.

In the instant reaction the starting group is the carboxylic acid which may esterified and then converted to the amide, or the amide may be prepared directly if the substituents on the remainder of the molecule would allow.

The ester is prepared with ethanol in the presence of an acid as described in the esterification previously described.

The amide is prepared with an appropriately substituted amine and a catalytic amount of a base such as an alkali metal alkoxide. The reaction is carried out in a solvent such as a lower alkanol at from 25° to 80° C. If temperatures higher than the boiling point of the reaction mixture are called for, a pressurized vessel may be employed. The reaction is generally complete in from 12 to 36 hours.

The amide is then reduced to prepare the substituted amino methyl group. The reducing agent may be lithium aluminum hydride, borane, and the like and is carried out in a solvent such as ether, tetrahydrofuran, and the like and is generally complete in from 2 to 6 hours. The products are isolated using techniques known to those skilled in the art.

EXAMPLE 1

N-Cyano-N'-[2-(6-dimethylaminomethyl-2-benzofuranylmethylthio)ethyl]-N"-methylguanidine A. Ethyl 6-Methylbenzofuran-2-carboxylate A solution of 6-methylbenzofuran-2-carboxylic acid (111.0 g., 0.636 mole) and concentrated sulfuric acid (4 ml.) in ethanol (1 l.) is boiled under reflux for 16 hours. About ⅔ of the solvent is removed by distillation at reduced pressure. The residue is poured into 1 l. of ice water. The oily ester is taken up in ether, washed with saturated sodium bicarbonate solution and water and dried over sodium sulfate. Distillation at reduced pressure affords 90.5 g. (70%) of ethyl 6-methylbenzofuran-2-carboxylate, b.p. 174°–176° C. (17 mm.). The product crystallizes in the receiver, m.p. 35°–42° C.

B. Ethyl 6-(bromomethyl)benzofuran-2-carboxylate

N-Bromosuccinimide (37.4 g., 0.21 mole) is added to a solution of ethyl-6-methylbenzofuran-2-carboxylate (40.8 g., 0.2 mole) and α,α'-azobisisobutyronitrile (500 mg.) in carbon tetrachloride (300 ml.). The suspension is boiled under reflux for 3 hours. It is then cooled and the succinimide removed by filtration. The carbon tetrachloride solution is washed with water and dried over sodium sulfate. The solution is then evaporated at reduced pressure. The solid residue is recrystallized from hexane to yield 47.4 g. (69%) of crystalline ethyl 6-(bromomethyl)benzofuran-2-carboxylate, m.p. 95°–102° C. NMR (CDCl$_3$): δ1.40 (3H,t,CH$_3$), 4.40(2H,q,CH$_2$O), 4.58 (2H, s,CH$_2$Br).

C. Ethyl 6-(dimethylaminomethyl)benzofuran-2-carboxylate

A solution of ethyl 6-(bromomethyl)benzofuran-2-carboxylate (47.0 g., 0.166 mole) in ether (75 ml.) is added during 30 minutes to a stirred solution of dimethylamine (18.9 g., 0.42 mole) in ether (100 ml.). The temperature is kept at 0°–5° C. during the addition by means of an ice bath. The mixture is then stirred for 30 minutes without being cooled. The precipitated dimethylamine hydrobromide is removed by filtration. The ether solution is extracted with 400 ml. of 5% hydrochloric acid. The aqueous solution is made basic by the addition of 40% sodium hydroxide solution. The liberated amine is taken up in ether and dried over sodium sulfate. Evaporation of the solvent leaves as an oily residue 36.2 g. (88%) of ethyl 6-(dimethylaminomethyl)benzofuran-2-carboxylate. NMR (CDCl$_3$): δ1.40 (3H, t,CH$_3$CH$_2$),2.26(6H,s,CH$_3$N),3.53(2H,s,CH$_2$N), 4.43(2H, q, CH$_2$O).

D. 6-(Dimethylaminomethyl)-2-benzofuranmethanol

Ethyl 6-(dimethylaminomethyl)benzofuran-2-carboxylate (36.1 g., 0.146 mole) in ether (150 ml.) is added dropwise during 1 hour to a stirred suspension of lithium aluminum hydride (5.5 g., 0.146 mole) in ether (150 ml.). The mixture is then cooled in an ice bath and treated successively with 5.7 ml. of water, 5.7 ml. of 15% sodium hydroxide solution and 17 ml. of water. The precipitated white solid is removed by filtration. The ether solution is evaporated to give 29.6 g. of a crystalline residue of 6-(dimethylaminomethyl)-2-benzofuranmethanol, m.p. 78.5°–80° C.

E. 2-(2-Aminoethylthiomethyl)-6-(dimethylaminomethyl)-benzofuran 6-(Dimethylaminomethyl)-2-benzofuranmethanol (28.3 g., 0.138 mole) is added to an ice-cold solution of cysteamine hydrochloride (17.2 g., 0.151 mole) in concentrated hydrochloric acid (70 ml.). The resulting solution is allowed to stand at room temperature for 45 hours. It is then cooled in an ice bath and made strongly basic by the addition of 10 N sodium hydroxide solution. The product is extracted with five portions of methylene chloride. The extracts are combined, washed with water and dried over Na$_2$SO$_4$. Evaporation of the solvent leaves 29.8 g. (82%) of 2-(2-aminoethylthiomethyl)-6-(dimethylaminomethyl)-benzofuran as an orange viscous oil. NMR (CDCl$_3$): δ1.70 (2H, br s, NH$_2$), 2.22 (6H, s, CH$_3$N), 2.65–2.9 (4H, m, SCH$_2$CH$_2$N), 3.44 (2H, s, PhCH$_2$N), 3.75 (2H, s, PhCH$_2$S), 6.45 (1H, s, furan H).

F. N-Cyano-N'-[2-(6-dimethylaminomethyl-2-benzofuranylmethylthio)ethyl]-S-methylisothiourea A solution of 2-(2-aminoethylthiomethyl)-6-(dimethylaminomethyl)benzofuran (12.0 g, 0.0454 mole) and dimethyl cyanodithioimidocarbonate (7.0 g., 0.048 mole) in acetonitrile (48 ml.) is allowed to stand 2 hours at room temperature. The solvent is evaporated at reduced pressure and the viscous oily residue is chromatographed on a column of 250 g. of silica gel. Elution with 8% methanol in chloroform removes the product. There is obtained 14.6 g. (89%) of N-cyano-N'-[2-(6-dimethylaminomethyl-2-(benzofuranylmethylthio)ethyl]-S-methylisothiourea as a yellow oil which gradually crystallizes, m.p. 98°–100° C.

G. N-Cyano-N'-[2-(6-dimethylaminomethyl-2-benzofuranylmethylthio)ethyl]-N''-methylguanidine A solution of N-cyano-N'-[2-(6-dimethylaminomethyl-2-benzofuranylmethylthio)ethyl]-S-methylisothiourea (8.8 g., 0.024 mole) and methylamine (31 g.) in ethanol (90 ml.) is allowed to stand at room temperature for 3 hours. The solvent is evaporated at reduced pressure. The residual oil gradually crystallizes, m.p. 62°–65° C. Two crystallizations of this product from acetonitrile-ether gives 7.0 g, (84%) of N-cyano-N'-[2-(6-dimethylaminomethyl-2-benzofuranylmethylthio)ethyl]-N''-methylguanidine as white needles, m.p. 115.5°–117.5° C.

EXAMPLE 2

N-Cyano-N'-[2-(7-dimethylaminomethyl-2-benzofuranylmethylthio)ethyl]-N''-methylguanidine This compound is prepared by the series of reactions described in Example I except that in Step A 7-methylbenzofuran-2-carboxylic acid is substituted for the 6-methylbenzofuran-2-carboxylic acid used in Example 1. The compounds thus obtained are:

Step A—Ethyl 7-methylbenzofuran-2-carboxylate, b.p. 164° C./18 mm. Hg.

Step B—Ethyl 7-bromomethyl)benzofuran-2-carboxylate, m.p. 81°–83° C.

Step C—Ethyl 7-(dimethylaminomethyl)benzofuran-2-carboxylate

Step D—7-(Dimethylaminomethyl)-2-benzofuranmethanol

Step E—2-(2-Aminoethylthiomethyl)-7-(dimethylaminomethyl)benzofuran

Step F—N-Cyano-N'-[2-(7-dimethylaminomethyl-2-benzofuranylmethylthio)ethyl]-S-methylisothiourea Step G—N-Cyano-N'-[2-(7-dimethylaminomethyl-2-benzofuranylmethylthio)ethyl]-N''-methylguanidine, m.p. 103.5°–105.5° C.

EXAMPLE 3

N-Cyano-N'-[2-(5-dimethylaminomethyl-2-benzofuranylmethylthio)ethyl]-N''-methylguanidine This compound is prepared by the series of reactions described in Example 1 except that in Step A 5-methylbenzofuran-2-carboxylic acid is substituted for the 6-methylbenzofuran-2-carboxylic acid used in Example 1. The compounds thus obtained are:

Step A—Ethyl 5-methylbenzofuran-2-carboxylate
Step B—Ethyl 5-(bromomethyl)benzofuran-2-carboxylate
Step C—Ethyl 5-(dimethylaminomethyl)benzofuran-2-carboxylate
Step D—5-(Dimethylaminomethyl)-2-benzofuranmethanol
Step E—2-(2-Aminoethylthiomethyl)-5↑-(dimethylaminomethyl)benzofuran
Step F—N-Cyano-N'-[2-(5-dimethylaminomethyl-2-benzofuranylmethylthio)ethyl]-S-methylisothiourea
Step G—N-Cyano-N'-[2-(5-dimethylaminomethyl-2-benzofuranylmethylthio)ethyl]-N''-methylguanidine

EXAMPLE 4

N-Cyano-N'-[2-(4-dimethylaminomethyl-2-benzofuranylmethylthio)ethyl]-N''-methylguanidine This compound is prepared by the series of reactions described in Example 1 except that in Step A 4-methylbenzofuran-2-carboxylic acid is substituted for the 6-methylbenzofuran-2-carboxylic acid used in Example 1. The compounds thus obtained are:

Step A—Ethyl 4-methylbenzofuran-2-carboxylate
Step B—Ethyl 4-(bromomethyl) benzofuran-2-carboxylate
Step C—Ethyl 4-(dimethylaminomethyl)benzofuran-2-carboxylate
Step D—4-(Dimethylaminomethyl)-2-benzofuranmethanol
Step E—2-(2-Aminoethylthiomethyl)-4-(dimethylaminomethyl)benzofuran
Step F—N-Cyano-N'-[2-(4-dimethylaminomethyl-2-benzofuranylmethylthio)ethyl]-S-methylisothiourea
Step G—N-Cyano-N'-[2-(4-dimethylaminomethyl-2-benzofuranylmethylthio)ethyl]-N''-methylguanidinee

EXAMPLE 5

N-Cyano-N'-[4-(6-dimethylaminomethyl-2-benzofuranyl)-butyl]-N''-methylguanidine

A. 2-(4-Bromobutyl)benzofuran-6-carboxylic acid n-Butyllithium solution (2.29 M in hexane, 44 ml., 0.1 mole) is added to a solution of diisopropylamine (10.1 g., 0.1 mole) in tetrahydrofuran (150 ml.) and hexamethylphosphoramide (15 ml.). The resulting solution is treated with benzofuran-6-carboxylic acid (8.1 g., 0.05 mole) and then with 1,4-dibromobutane (10.8 g., 0.05 mole) at 0° C. The mixture is stirred at 0° C. for 6 hours. It is then quenched with water, acidified with hydrochloric acid and extracted with ethyl acetate. Evaporation of the solvent gives 2-(4-bromobutyl)benzofuran-6-carboxylic acid.

B. Ethyl 2-(4-bromobutyl)benzofuran-6-carboxylate

A solution of 2-(4-bromobutyl)benzofuran-6-carboxylic acid (29.7 g., 0.1 mole) and sulfuric acid (0.5 ml.) in ethanol (200 ml.) is boiled under reflux. The solution is concentrated to ⅔ volume at reduced pressure. The residue is poured into water. The oily ester is extracted with ether. Evaporation of the solvent provides ethyl 2-(4-bromobutyl)benzofuran-6-carboxylate.

C. Ethyl 2-(4-phthalimidobutyl)benzofuran-6-carboxylate

A solution of ethyl 2-(4-bromobutyl)benzofuran-6-carboxylate (3.25 g., 0.01 mole) and potassium phthalimide (2.04 g., 0.011 mole) in dimethylformamide (25 ml.) is stirred at 25°–27° C. for 18 hours. The solution is poured into water. The precipitated ethyl 2-(4-phthalimidobutyl)benzofuran-6-carboxylate is collected by filtration.

D. Ethyl 2-(4-aminobutyl)benzofuran-6-carboxylate

A solution of ethyl 2-(4-phthalimidobutyl)-benzofuran-6-carboxylate (3.9 g., 0.01 mole) and hydrazine hydrate (0.55 g., 0.011 mole) in ethanol (20 ml.) is heated at 60° C. for 8 hours. The solvent is evaporated at reduced pressure. The solid residue is treated with water and 5 N sodium hydroxide solution and then is extracted with chloroform. The evaporation of the solvent from the organic extract provides ethyl 2-(4-aminobutyl)benzofuran-6-carboxylate.

E. N,N-Dimethyl-2-(4-aminobutyl)benzofuran-6-carboxamide

A solution of ethyl 2-(4-aminobutyl)benzofuran-6-carboxylate (13.0 g., 0.05 mole), dimethylamine (35 g.), and a catalytic amount of sodium ethoxide (approximately 100 mg.) in ethanol (100 ml.) is heated in a sealed pressure bottle at 65° C. for 18 hours. Evaporation of the solvent provides N,N-dimethyl-2-(4-aminobutyl)-benzofuran-6-carboxamide.

F. 2-(4-Aminobutyl)-6-(dimethylaminomethyl)benzofuran

N,N-dimethyl-2-(4-aminobutyl)benzofuran-6-carboxamide (13.0 g., 0.05 mole) in tetrahydrofuran (60 ml.) is added dropwise with stirring to lithium aluminum hydride (3.0 g., 0.08 mole) in tetrahydrofuran (60 ml.) at 25°–30° C. The mixture is stirred for 2 hours at 25°–30° C. and then is treated successively with 3 g. of water, 3 g. of 15% sodium hydroxide solution and 9 g. of water. The solid precipitate is removed by filtration. The tetrahydrofuran solution is evaporated at reduced pressure to provide 2-(4-aminobutyl)-6-dimethylaminomethyl)-benzofuran.

G. N-Cyano-N'-[4-(6-dimethylaminomethyl-2-benzofuranyl)-butyl]-S-methylisothiourea This compound is obtained by the reaction of 2-(4-aminobutyl)-6-(dimethylaminomethyl)benzofuran with dimethyl cyanodithioimidocarbonate following the procedure described in Example 1, Step F.

H. N-Cyano-N'-[4-(6-dimethylaminomethyl-2-benzofuranyl)butyl]-N''-methylquanidine This compound is obtained by the reaction of N-cyano-N'-[4-(6-dimethylaminomethyl-2-benzofuranyl)-butyl]-S-methylisothiourea with methylamine following the procedure described in Example 1, Step G.

EXAMPLE 6

N-Cyano-N'-[2-(6-diethylaminomethyl)-2-benzofuranylmethylthio)ethyl]-N''-methylguanidine This compound is prepared by the series of reactions described in Example 2 except that in Step C diethylamine is substituted for the dimethylamine used in Example 2, Step C. The subsequent compounds thus obtained are:

Step C—Ethyl 6-(diethylaminomethyl)benzofuran-2-carboxylate
Step D—6-(Diethylaminomethyl)-2-benzofuranmethanol
step E—2-(2-Aminoethylthiomethyl)-6-(diethylaminomethyl)benzofuran
Step F—N-Cyano-N'-[2-(6-diethylaminomethyl-2-benzofuranylmethylthio)ethyl]-S-methylisothiourea
Step G—N-Cyano-N'-[2-(6-diethylaminomethyl)-2-benzofuranylmethylthio)ethyl]-N''-methylguanidine

EXAMPLE 7

N-Cyano-N'-[2-(6-(1-piperidinyl)methyl-2-benzofuranylmethylthio)ethyl]-N''-methylguanidine This compound is prepared by the series of reactions described in Example 1 except that in Step C an equivalent quantity of piperidine is substituted for the dimethylamine in Example 1, Step C. The subsequent compounds thus obtained are:

Step C—Ethyl 6-[(1-piperidinyl)methyl]benzofuran-2-carboxylate
Step D—6-[(1-Piperidinyl)methyl]-2-benzofuranmethanol
Step E—2-(2-Aminoethylthiomethyl)-6-[(1-piperidinyl)-methyl]benzofuran
Step F—N-Cyano-N'-[2-(6-(1-piperidinyl)methyl-2-benzofuranylmethylthio)ethyl]-S-methylisothiourea
Step G—N-Cyano-N'-[2-(6-(1-piperidinyl)methyl-2-benzofuranylmethylthio)ethyl]-N''-methylguanidine

EXAMPLE 8

N-[2-(6-Dimethylaminomethyl-2-benzofuranylmethylthio)-ethyl]-N'-methyl-2-nitro-1,1-ethenediamine

A.

N-[2-(6-Dimethylaminomethyl-2-benzofuranylmethylthio)-ethyl]-1-methylthio-2-nitroetheneamine A solution of 2-(2-aminoethylthiomethyl)-6-(dimethylaminomethyl)benzofuran (Example 1, Step E) (8.0 g., 0.0303 mole) and 1,1-bismethylthio-2-nitroethene (5.25 g., 0.0318 mole) in acetonitrile (80 ml.) is heated at 55° C. for 16 hours. The solvent is evaporated at reduced pressure. The residue is chromatographed on a column containing 175 g. of silica gel made up in chloroform. The product is eluted with 5% methanol in chloroform and is obtained as a light orange viscous oil weighing 6.1 g. (53%).

B.

N-[2-(6-Dimethylaminomethyl-2-benzofuranylmethylthio)-ethyl]-N'-methyl-2-nitro-1,1-ethenediamine A solution of N-[2-(6-dimethylaminomethyl-2-benzofuranylmethylthio)ethyl]-1-methylthio-2-nitroetheneamine (6.0 g., 0.0157 mole) and methylamine (20 g.) in ethanol (60 ml.) is allowed to stand 2 hours at 27° C. The solvent was evaporated at reduced pressure. The solid residue is recrystallized from acetonitrile-ether to yield 3.1 g. (54%) of N-[2-(6-dimethylaminomethyl-2-benzofuranylmethylthio)ethyl]-N'-methyl-2-nitro-1,1-ethenediamine, m.p. 113°–114° C.

The products in the following table are prepared by the method of Step B of this Example except that methylamine is replaced by the appropriate amine $R_3NH_2$ in the threefold or greater molar excess:

| | |
|---|---|
| $R_3$ | M.P. °C. |
| —$CH_2C\equiv CH$ | 155–156 |
| —$CH_2CH=CH_2$ | 105–107 |
| —$CH_2$—⟨phenyl⟩ | 148–149 |
| —$CH_2CH_2$—⟨phenyl⟩ | 114–116 |
| —$CH_2CH_2OH$ | 125–128 |
| —$CH_2CH_2$—$OCH_3$ | 115–116 |
| —$CH_2CH_2$—$N(CH_3)_2$ | 89–90 |
| —⟨cyclopropyl⟩ | |
| —$CH_2$—⟨cyclopropyl⟩ | 109–112 |

EXAMPLE 9

N-Cyano-N'-[2-(6-dimethylaminomethyl-2-benzofuranylmethylthio)ethyl]guanidine

A solution of N-cyano-N'-[2-(6-dimethylaminomethyl)-2-benzofuranylmethylthio)ethyl]-S-methylisothiourea (Example 1, Step F) (6.27 g., 0.0173 mole) and ammonia (12 g.) in ethanol (65 ml.) is heated in a sealed vessel for 36 hours at 55°–60° C. Volatile materials are then removed by distillation at reduced pressure. The residual oil consisting of the nearly pure product is purified by column chromatography on 85 g. of silica gel with elution by a 10% solution of methanol in chloroform affording N-cyano-N'-[2-(6-dimethylaminomethyl-2-benzofuranylmethylthio)ethyl]-guanidine.

EXAMPLE 10

N-Cyano-N'-[2-(6-dimethylaminomethyl-2-benzofuranylmethylthio)ethyl]-N''-(2-propynyl)guanidine A solutiion of N-cyano-N'-[2-(6-dimethylaminomethyl)-2-benzofuranylmethylthio)ethyl]-S-methylisothiourea (Example 1, Step F) (6.55 g., 0.018 mole) and propargylamine (4.0 g., 0.073 mole) in acetonitrile (100 ml.) is heated in a sealed pressure vessel at 110°–120° C. for 36 hours. The reaction solution is then evaporated at reduced pressure. N-cyano-N'-[2-(6-dimethylaminomethyl-2-benzofuranylmethylthio)ethyl]-N''-(2-propynyl)guanidine is obtained when the residual oil is chromatographed on silica gel with elution by an 8% solution of methanol in chloroform.

EXAMPLE 11

N-Benzyl-N'-cyano-N''-[2-(6-dimethylaminomethyl-2-benzofuranylthio)ethyl[guanidine This compound is prepared by the procedure described in Example 10 except that an equivalent quantity of benzylamine is substituted for the propargylamine used in Example 10.

EXAMPLE 12

N-[2-(6-Dimethylaminomethyl-2-benzofuranylmethylthio)-ethyl]-N'-(2-propenyl)thiourea A solution of 2-(2-aminoethylthiomethyl)-6-(dimethylaminomethyl)benzofuran (Example 1, Step E) (2.6 g., 0.01 mole) and allyl isothiocyanate (1.1 g., 0.011 mole) in acetonitrile (15 ml.) is kept at 25°–27° C. for 16 hours. The solvent is evaporated and the residual oil chromatographed (silica gel/5% methanol in chloroform) to yield N-[2-(6-dimethylaminomethyl-2-benzofuranylmethylthio)ethyl]-N'-(2-propenyl)thiourea.

EXAMPLE 13

N-[2-(6-Dimethylaminomethyl-2-benzofuranylmethylthio)-ethyl]-N'-nitroguanidine A solution of 2-(2-aminoethylthiomethyl)-6-(dimethylaminomethyl)benzofuran (Example 1, Step E) (2.6 g., 0.01 mole) and S-methyl-N-nitroisothiourea (1.4 g., 0.01 mole) in acetonitrile (15 ml.) is kept at 25°–27° C. for 4 hours. The solvent is evaporated and the residue chromatographed on silica gel (5% methanol in chloroform elution) to yield N-[2-(6-dimethylaminomethyl-2-benzofuranylmethylthio)ethyl]-N'-nitroguanidine.

EXAMPLE 14

N-[2-(6-Dimethylaminomethyl-2-benzofuranylmethylthio)-ethyl]-N'-methanesulfonyl-N''-methylguanidine A solution of 2-(2-aminoethylthiomethyl)-6-(dimethylaminomethyl)benzofuran (Example 1, Step E) (2.6 g., 0.01 mole) and methanesulfonyliminodithiocarbonic acid dimethyl ester (2.0 g., 0.01 mole) in methanol (15 ml.) is kept at 25°–27° C. for 4 hours. A solution of 10 g. of methylamine in 35 ml. of methanol is added and the resulting solution is kept at 25°–27° C. for 16 hours. The solvent is evaporated to leave N-[2-(6-dimethylaminomethyl-2-benzofuranylmethylthio)-ethyl]-N'-methanesulfonyl-N''-methylguanidine as a residual oil which is purified by column chromatography (silica gel/5% methanol in chloroform).

EXAMPLE 15

N-Cyano-N'-[3-(6-dimethylaminomethyl-2-benzofuranylmethylthio)propyl]-N''-methylguanidine This compound is prepared by the series of reactions described in Example 1 except that in Step E an equivalent amount of 3-amino-1-propanethiol hydrochloride is substituted for the cysteamine hydrochloride employed in Example 1, Step E. The subsequent compounds thus obtained are:

Step E—2-(3-Aminopropylthiomethyl)-6-(dimethylaminomethyl)benzofuran

Step F—N-Cyano-N'-[3-(6-dimethylaminomethyl-2-benzofuranylmethylthio)propyl]-S-methylisothiourea Step G—N-Cyano-N'-[3-(6-dimethylaminomethyl-2-benzofuranylmethylthio)propyl]-N''-methylguanidine

What is claimed is:

1. A compound having the formula:

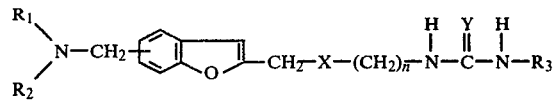

wherein $R_1$ and $R_2$ are independently loweralkyl of from 1 to 3 carbon atoms, and $R_1$ and $R_2$ may be joined to form, together with the nitrogen atom to which they are attached, heterocycle selected from piperidine, pyrrolidine, morpholine, piperazine, and N-methylpiperazine;

X is sulfur or a methylene group;

n is 2, 3, or 4;

$R_3$ is hydrogen, lower alkyl, cycloloweralkyl, cycloloweralkyl lower alkyl, loweralkenyl, loweralkynyl, phenylloweralkyl, hydroxyloweralkyl, loweralkoxyloweralkyl, and di(loweralkyl)aminoloweralkyl; and Y is sulfur, $=CHNO_2$ or $=NR_4$ wherein $R_4$ is nitro, cyano, or loweralkylsulfonyl.

2. The compound of claim 1 wherein the heterocycle is piperidine or pyrrolidine.

3. The compound of claim 1 wherein:
$R_1$ and $R_2$ are the same and are loweralkyl of from 1 to 3 carbon atoms;
X is sulfur;
n is 2;
$R_3$ is hydrogen, loweralkyl, or loweralkynyl; and
Y is $=CHNO_2$ or $=N$-CN.

4. The compound of claim 3 wherein:
$R_1$ and $R_2$ are methyl;
X is sulfur;
n is 2;
$R_3$ is hydrogen, methyl, ethyl or propargyl; and
Y is $=CH$-$NO_2$ or $=N$-CN.

5. The compound of claim 4 wherein:
$R_1$ and $R_2$ are methyl;
X is sulfur;
n is 2;
$R_3$ is hydrogen or methyl; and
R is $=CH$-$NO_2$ or $=N$-CN.

6. The compound of claim 5 which is N-cyano-N'-[2-(6-dimethylaminomethyl-2-benzofuranylmethylthio)-ethyl]-N''-methyl-guanidine.

7. The compound of claim 5 which is N-[2-(6-dimethylaminomethyl-2-benzofuranylmethylthio)ethyl]-N'-methyl-2-nitro-1,1-ethenediamine.

8. A method for the treatment of excess gastric acid secretions which comprises administering to a mammal with excess gastric acid secretions, an effective amount of a compound of claim 1.

9. A composition useful for the treatment of excess gastric acid secretions which comprises an inert carrier and an effective amount of a compound of claim 1.

* * * * *